United States Patent [19]

Martin et al.

[11] Patent Number: 4,938,959
[45] Date of Patent: Jul. 3, 1990

[54] INSOLUBLE MEDICAMENT FOR A LOCAL ADMINISTRATION IN A HUMAN OR ANIMAL EAR

[75] Inventors: Henri A. Martin; Maurice Carraz; René Mallein, all of Lyon; Georges S. Grimberg, 123 rue de l'Université, Paris, all of France

[73] Assignee: Georges Serge Grimberg, Paris, France

[21] Appl. No.: 239,340

[22] Filed: Aug. 30, 1988

Related U.S. Application Data

[63] Continuation-in-part of Ser. No. 797,684, Nov. 13, 1985, abandoned.

[30] Foreign Application Priority Data

Nov. 14, 1984 [FR] France .................. 84 17397

[51] Int. Cl.$^5$ ............................................... A61K 35/00
[52] U.S. Cl. ..................................... 424/114; 424/120
[58] Field of Search ............................... 424/114, 120

[56] References Cited

U.S. PATENT DOCUMENTS 2,797,183  6/1957  Hazen et al. .................. 424/120

Primary Examiner—Jerome D. Goldberg
Attorney, Agent, or Firm—Browdy and Neimark

[57] ABSTRACT

An ear powder and/or drop, containing soluble substances and an insoluble substance which will be spread of the mucous membrane and form a deposit which will act by its physical acitivity as a dilution support for powder active principles and as a sponge for drops.

6 Claims, No Drawings

INSOLUBLE MEDICAMENT FOR A LOCAL ADMINISTRATION IN A HUMAN OR ANIMAL EAR

This application is a continuation-in-part of application Ser. No. 797,684, filed Nov. 13, 1985, now abandoned.

FIELD OF THE INVENTION

All the ear drops used up to now are perfect solutions of various completely soluble substances. of various completely soluble substances.

Therefore, they have only a limited action with time since they do not remain, they flow out from the ear after having been more or less into contact with a ill ear mucous membrane.

OBJECT AND SUMMARY OF THE INVENTION

The present invention has for its object to use an insoluble substance and to locally administer this substance in a human or animal ear in order to form a deposit regularly spread on the mucous membrane and which will act through its physical activity either as a diluting support of powder active principles (e.g.) or as a sponge, or which could also act by its own therapeutic activity (e.g. nystatin).

To this insoluble substance will therefore be associated: pharmaceutically antiseptic and/or antibiotic and/or anti-inflammatory substances.

The volume in powder obtained by the insoluble substance and the other substances will be substantially the same as the volume obtained by adding a certain amount of physiological solution. Therefore, the solid or liquid dilution of substances such as antiseptic and/or antibiotic and/or anti-inflammatory substances will be the same.

The insoluble substance should be suitably tolerated by the ear.

The insoluble substance which corresponds to these various needs and permits to obtain the present ear powder-drop is a product called "nystatin".

This substance maintains in place either powdered diluted active principles, or a solution of active principles.

It is obviously possible to choose another powder and to use, further to antibiotics, a soluble antifongic substance.

According to a first aspect of the invention, the insoluble medicament is a ear powder and drop containing soluble substances and an insoluble substance which will be spread on the mucous membrane and form a deposit which will act by its physical activity as a dilution support for powder active principles and as a sponge for drops.

According to a second aspect of the invention, the insoluble medicament is a powder containing soluble substances and an insoluble substance which will be spread on the mucous membrane and form a deposit which will act by its physical activity as a dilution support.

According to a third aspect of the invention, the insoluble medicament is an ear drop containing soluble substances and an insoluble substance which will be spread on the mucous membrane and form a deposit which will act as a sponge.

Various other features of the invention will be moreover revealed from the following detailed disclosure.

EXAMPLES OF COMPOSITIONS

There are given hereinafter examples of compositions of insoluble medicament to be locally administered in a human or animal ear. These examples are intended to be illustrative only, and not limiting.

Example No. 1

Antibiotics: q.s. for therapeutic activity
Antiinflammatory substance: q.s. for therapeutic activity
Nystatin in fine powder: q.s. for 10 ml

Example No. 2

Antibiotics: q.s. for therapeutic activity
Antiinflammatory substance q.s. for therapeutic activity
Nystatin in powder: q.s. for 10 ml
Physiological solution: 10 ml Examples of use are numerous. Thus, the examples mentioned hereinunder are exemplitive only and it should be that it is possible to employ the method of the present invention to substitute for practically all the otic solutions cited in USP XXI, incorporated herein by reference.

Example No. 3

| Soluble part: | Bacitracin | 10,000 units |
|---|---|---|
| | Neomycin | 50 mg |
| | Polymyxin B sulphate | 100,000 units |
| Insoluble part: | Nystatin $10^6$ units | (200 mg) |

The composition may be applied by powdering into the ear 3–4 times a day, or by adding 10 ml of physiological serum (i.e. physiological isotonic and isomatic saline solution) and using, after stirring, 2–3 drops, 3–4 times a day.

Example No. 4

| Soluble part: | Polymyxin B sulphate | 100,000 units |
|---|---|---|
| | Neomycin sulphate | 3 400 units |
| | Hydrocortisone | 100 mg |
| Insoluble part: | Nystatin $10^6$ units | (200 mg) |

The composition may be applied by powdering into the ear 3–4 times a day, or by adding 10 ml of physiological serum and using, after stirring, 2–3 drops, 3–4 times a day.

Example No. 5

| Soluble part: | Cloxacillin sodium | 0.1 g |
|---|---|---|
| | Phenyl mercuric nitrate | 0.0002 g |
| Insoluble part: | Nystatin $10^6$ units | (200 mg) |

The composition may be applied by powdering into the ear 3–4 times a day, or by adding 10 ml of physiological serum and using, after stirring, 2–3 drops, 3–4 times a day.

Example No. 6

| Soluble part: | Rifamycin sodium | 0.28 g |

| | |
|---|---|
| -continued | |
| Insoluble part: Nystatin 10⁶ units | (200 mg) |

The composition may be applied by powdering into the ear 3-4 times a day, or by adding 10 ml of physiological serum and using, after stirring, 2-3 drops, 3-4 times a day.

Example No. 7

| | | |
|---|---|---|
| Soluble part: | Chlorhexidine acetate | 5 mg |
| Insoluble part: | Nystatin 10⁶ units | (200 mg) |

The composition may be applied by powdering into the ear 3-4 times a day, or by adding 10 ml of physiological serum and using, after stirring, 2-3 drops, 3-4 times a day.

It should be noted that the amount of nystatin represents a volume of "solid dilution" which gives a non-toxic concentration of the antibiotics. The particle size of the nystatin must be adapted for providing a final volume of the "soluble-insoluble" product, which is about 10 ml, as well as the appropriate nystatin activity. Actually, if the soluble part is powdered into the ear without diluting it in the insoluble part, the product will be toxic for the ear.

Of course, the particle size of any therapeutically active diluent must be adjusted to provide an appropriate volumetric dilution of the active ingredient along with a therapeutic dose of the solid diluent. Also, the particle size of therapeutically inactive diluents can to some extent determine the degree of homogeneity and dilution in the final composition, often resulting from absorption of active component on the surface of the diluent. In other words, if the particle size is too large, then the active therapeutic agent, if absorbed on the surface of the diluent, is actually distributed over a rather small surface area, and the degree of dilution (as measured by therapeutic activity) provided by a volume of solid diluent will be less than that provided by the same volume of physiological saline. Likewise, if the diluent particles are too small, the active therapeutic agent will be distributed over a rather large surface area of diluent particles and exhibit the therapeutic activity of a more dilute solution of active therapeutic agent in physiological saline.

In the above examples, the particle sizes of nystatin are essentially uniform. Therefore, a range of appropriate particle sizes for diluents may be obtained by reference to the activity and weight recited. Also, by varying the particle size, those skilled in the art can observe the best particles sizes for each diluent.

Now, with respect to the amount of product to be administered into the ear of a patent, the amount is that used therapeutically in this field.

EXPERIMENTATION

Experimentation on animal

The toxicity and the pharmacology have revealed nothing abnormal and give the foreseen results, i.e.: the medicament formed by nystatin, an antibiotic and an antiinflammatory product is not toxic.

Experimentation on human

The study has been made in double-blind and comprises a comparaison of six products on 120 ill persons having a chronical otitis.

| | PRODUCTS No | | | | | |
|---|---|---|---|---|---|---|
| | 1 | 2 | 3 | 4 | 5 | 6 |
| ANTIBIOTICS | + | + | + | + | + | + |
| ANTI-INFLAMMATORY SUBSTANCE | 0 | + | 0 | + | 0 | + |
| NYSTATIN | 0 | 0 | + | + | + | + |
| PHYSIOLOGICAL SERUM | + | + | + | + | 0 | 0 |

Products No. 4 et 6 have been found to give the best results.

Products No. 3 et 5 can be compared together and give better results than products 1 and 2.

We claim:

1. A method of treating an ear canal comprising applying to said ear canal a composition comprising an otically active therapeutic agent, soluble in physiological solution, in an amount therapeutically effective to treat said ear canal, mixed with an amount of nystatin, effective to dilute said otically active therapeutic agent to a non-toxic but therapeutically effective concentration, said active therapeutic agent being absorbable by said diluent.

2. The method of claim 1, wherein said therapeutically active substance is an antibiotic or an anti-inflamatory medication.

3. The method of claim 2, wherein said therapeutically active substance is a mixture of an antibiotically effective amount of an antibiotic with an anti-inflammatory amount of an anti-inflammatory medication.

4. The method of claim 1, wherein said composition comprises a physiological solution of said active therapeutic agent, with said diluent suspended therein.

5. The method of claim 1, wherein said composition is applied to said ear canal in a dry solid form.

6. The method of claim 5, wherein said dry solid form is a powder.

* * * * *